United States Patent [19]

Durette

[11] 4,310,514

[45] Jan. 12, 1982

[54] IMMUNOLOGICALLY ACTIVE DIPEPTIDYL 5-0,6-0-ACYL-2-AMINO-2-DEOXY-D-GLUCOFURANOSE DERIVATIVES AND METHODS OF PREPARATION

[75] Inventor: Philippe L. Durette, New Providence, N.J.

[73] Assignee: Merck & Co., Inc., Rahway, N.J.

[21] Appl. No.: 146,806

[22] Filed: May 5, 1980

[51] Int. Cl.$^3$ .................... A61K 39/00; A61K 37/02; C07C 103/52

[52] U.S. Cl. .................... 424/88; 424/89; 424/92; 424/85; 424/177; 260/112.5 R

[58] Field of Search ................ 260/112.5 R; 422/177; 424/88-92, 85

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,101,536 | 7/1978 | Yamamura et al. | 260/112.5 R |
| 4,101,649 | 7/1978 | Adams | 260/112.5 R |
| 4,153,684 | 5/1979 | Audibert et al. | 260/112.5 R |

FOREIGN PATENT DOCUMENTS

| | | |
|---|---|---|
| 821385 | 10/1974 | Belgium . |
| 834753 | 2/1976 | Belgium . |
| 834754 | 2/1976 | Belgium . |
| 847103 | 8/1977 | Belgium . |
| 849214 | 9/1977 | Belgium . |
| 7619236 | 6/1976 | France . |
| 7422909 | 5/1977 | France . |
| 52-46020 | 12/1977 | Japan . |

OTHER PUBLICATIONS

Elloys et al., Biochem. Biophys. Res: Commun., vol. 59, pp. 1317-1325 (1974).
Adam et al., Biochem. Biophys. Res. Commun., vol. 72, pp. 339-346 (1976).
Kotani et al., Biken Journal, vol. 18, 105-111 (1975).
Kusumoto et al., Tetrahedron Lett., 4407-4410 (1978).
Sharon et al., J. Biol. Chem. vol. 241, pp. 223-230, 1966.
Bogdanov et al., FEBS. Letters, vol. 57, pp. 259-261, 1975.
Merser et al., Tetrahedron Letters, vol. 13, pp. 1029-1032, 1973.
Takada et al., Biken J., vol. 20, pp. 81-85, 1977.
Audibert et al., Cellular Immunology, vol. 21, pp. 243-249, 1976.
Tanaska et al., Infection and Immunity, pp. 332-334, 1977.
Derment Abstract, No. 60347 4/34, Japanese Pat. No. 2083506, 1977.
Derment Abstract, No. 650114/37, Belgium Pat. No. 852348, 1977.
Derment Abstract, Japanese Pat. No. J52156-812, 1977.
Derment Abstract, Japanese Pat. No. J53077-011, 1978.
Derment Abstracts, French Pat. No. 2324311, 1977.
Derment Abstracts, Belgium Pat. No. 852349, 1977.
Derment Abstracts, German Pat. No. 2710452, 1977.
Derment Abstracts, New Zealand Pat. No. 7702-580, 1977.

Primary Examiner—Blondel Hazel
Attorney, Agent, or Firm—Donald J. Perrella; Raymond M. Speer; Hesna J. Pfeiffer

[57] ABSTRACT

Immunologically active compounds of the formula:

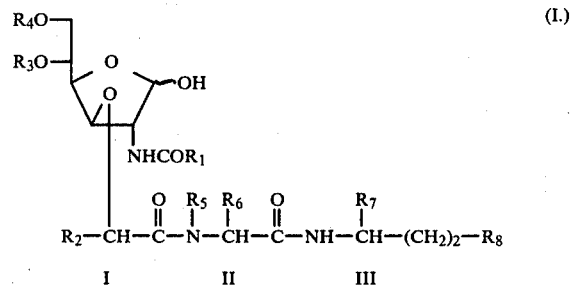

wherein $R_1$ is $C_{1-7}$ alkyl, substituted $C_{1-7}$ alkyl; phenyl; or substituted phenyl;

$R_2$ is hydrogen; or $C_{1-10}$ alkyl;

$R_3$ and $R_4$ may be the same or different and are each independently acyl of the formula:

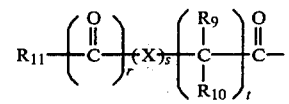

where
X is —O—, —S—, or

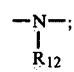

$R_9$, $R_{10}$ and $R_{12}$ may be the same or different and are each independently hydrogen; $C_{1-20}$ alkyl; $C_{1-20}$ alkylcarbonyloxy; amino; benzyl; $C_{1-20}$ alkoxymethyl; or $C_{1-20}$ alkylamido;

r is 0 or 1; s is 0 or 1; and t is 0-20, provided that s may only be 0 when r and t are greater than 0, or when r is 0 and $R_{11}$ is amino, phenyl, substituted phenyl, 1-adamantyl, or heterocycle selected from the group consisting of 2- or 3-furyl, 2- or 3-thienyl, 2- or 3-pyrrolidinyl, 2-, 3-, or 4-pyridyl, and 1-tetrazolyl, said hetero-cycle optionally substituted with $C_{1-20}$ alkylcarbonyl; and $R_{11}$ is hydrogen; $C_{1-30}$ alkyl; $C_{2-30}$ alkenyl; $C_{1-30}$ alkoxy; phenyl; $C_{1-20}$ alkylsulfonyl; or cholesteryl; and $R_4$ may additionally be hydrogen;

$R_5$ is hydrogen; or $R_5$-$R_6$ together is —CH$_2$—CH$_2$—CH$_2$;

$R_6$ is hydrogen; $C_{1-7}$ alkyl; hydroxymethyl; mercapto-methyl; benzyl; or substituted benzyl;

$R_7$ and $R_8$ may be the same or different and are each independently COOR or CONR'R", where R is hydrogen or $C_{1-7}$ alkyl, and R' and R" are each independently hydrogen or $C_{1-3}$ alkyl;

when $R_2$ is $C_{1-10}$ alkyl, the stereochemistry at asymmetric center I can be either D or L;

when $R_6$ is not hydrogen, the stereochemistry at asymmetric center Ii is L; the stereochemistry at asymmetric center III is D.

10 Claims, No Drawings

IMMUNOLOGICALLY ACTIVE DIPEPTIDYL 5-0,6-0-ACYL-2-AMINO-2-DEOXY-D-GLUCOFURANOSE DERIVATIVES AND METHODS OF PREPARATION

BACKGROUND OF THE INVENTION

1. Field of the Invention

The present invention is concerned with improved novel immunoadjuvants.

As is known in the field of immunology, multiple injections of a vaccine may be necessary to induce an immune response in a host sufficient to provide immunity because the viral or bacterial antigen contained in the vaccine is often cleared from the injection site too rapidly to permit an adequate immune response. Thus, immunological adjuvants have been added to vaccines in order to delay release of the viral or bacterial antigen and/or to stimulate the host's immunological response. However, many of the earlier immunological adjuvants which were employed had serious drawbacks, such as causing irritation at the site of injection. Accordingly, the art has long sought an immunological adjuvant which would be readily metabolized by the host without serious side effect, while at the same time delaying release of antigen and stimulating the immune response of the host.

One of the most active immunoadjuvants is Freund's Complete Adjuvant which is a water-in-oil emulsion consisting of 10% Arlacel A and 90% mineral oil containing whole killed mycobacterial cells. A vaccine is formulated with Freund's Complete Adjuvant by incorporating the antigen in the aqueous phase. Therapeutic applications of Freund's Complete Adjuvant, however, have been prevented due to accompanying toxic side effects such as local granulomas, endotoxic shock, and adjuvant-induced polyarthritis. The minimal active structure of mycobacteria has been determined by Ellouz et al., *Biochem. Biophys. Res. Commun.*, 59, 1317 (1974) and by Kotani et al., *Biken J.*, 18, 105 (1975) to be a peptidoglycan fragment of the cell wall, more specifically, a muramyl dipeptide, namely, N-acetylmuramyl-L-alanyl-D-isoglutamine (MDP). The addition of synthetic MDP to an emulsion of Freund's incomplete adjuvant (90% mineral oil and 10% Arlacel A) containing an antigen increases the level of antibodies against the antigen (humoral response) and induces delayed hypersensitivity (cellular immunity).

The effects of various structural modifications of the dipeptidyl moiety of MDP or biological activity have been reported, although studies on the effects of modifications of the saccharide moiety have been limited.

2. Brief Description of the Prior Art

Ellouz et al., *Biochem. Biophys. Res. Commun.*, 59, 1317–25 (1974) discloses that MDP is the minimal bacterial cell wall fragment having adjuvant activity.

Adam et al., *Biochem. Bioyphys. Res. Commun.* 72 339–346 (1976) discloses various lactyl dipeptide modifications of MDP. All were less active than MDP except N-acetyl-muramyl-L-seryl-D-isoglutamine which was as active as MDP.

Kotani et al., *Biken Journal*, 18, 105–111 (1975) discloses that MDP has adjuvant activity in saline solution as well as in water-in-oil emulsion.

U.S. Pat. Nos. 4,082,735 and 4,082,736 disclose various MDP analogs obtained by acetylating the sugar hydroxyl groups, varying the amino acid constituents of the dipeptides, using alkyl or aryl amide substituents, and varying the acid ether linkage between the sugar and the dipeptide.

Belgian Pat. Nos. 852,348 and 852,349 disclose N-acetylmuramyl dipeptides wherein the dipeptide is either L-alanyl-D-isoglutamine or L-seryl-D-isoglutamine, and their esters and amides.

Japanese Pat. Nos. 2083506 and 2046020 disclose N-acetylmuramyl dipeptides acylated with fatty acids at the 6-position of the sugar moiety.

Japanese Pat. No. J5-2156-812 discloses MDP acetylated in the 6-position with mycolic acid.

Japanese Pat. No. J5-3077-011 discloses an analog of the preceding compound wherein glycine is substituted for L-alanine in the dipeptide moiety.

Belgian Pat. Nos. 834,753 and 834,754 disclose oil-free adjuvant compositions containing MDP and an MDP analog wherein D-glutamic acid is substituted for D-isoglutamine.

Japanese Pat. No. 54-130,517 discloses MDP higher fatty acid esters in which the 6-O-position is substituted with $C_{1-90}$ acyl, optionally unsaturated, branched, or substituted, and optionally containing additional hydroxyl, carboxyl, carbonyl, amino, methoxy, or cyclopropyl functional groups.

SUMMARY OF THE INVENTION

In accordance with the present invention there are provided novel compounds of the formula:

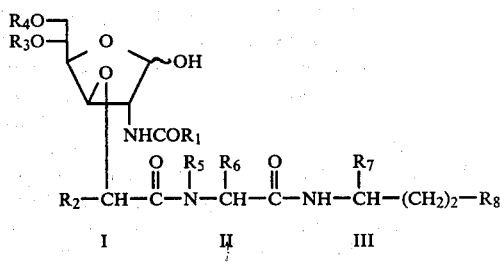

wherein:

$R_1$ is $C_{1-7}$ alkyl, substituted $C_{1-7}$ alkyl; phenyl; or substituted phenyl;

$R_2$ is hydrogen; or $C_{1-10}$ alkyl;

$R_3$ and $R_4$ may be the same or different and are each independently acyl of the formula:

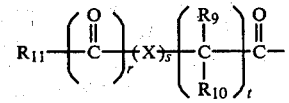

where

X is —O—, —S—, or

$R_9$, $R_{10}$, and $R_{12}$ may be the same or different and are each independently hydrogen; $C_{1-20}$ alkyl; $C_{1-20}$ alkylcarbonyloxy; amino; benzyl; $C_{1-20}$ alkoxymethyl; or $C_{1-20}$ alkylamido;

r is 0 or 1; s is 0 or 1; and t is 0–20, provided that s may only be 0 when r and t are greater than 0, or when r is 0 and $R_{11}$ is amino, phenyl, substituted phenyl, 1-adamantyl, or heterocycle selected from the group consisting of 2- or 3- furyl, 2- or 3- thienyl, 2- or 3-pyrrolidinyl, 2-, 3-, or 4-pyridyl, and 1-tetrazolyl, said heterocycle optionally substituted with $C_{1-20}$ alkylcarbonyl; and $R_{11}$ is hydrogen; $C_{1-30}$ alkyl; $C_{2-30}$ alkenyl; $C_{1-30}$ alkoxy; phenyl; $C_{1-20}$ alkysulfonyl; or cholesteryl; and $R_4$ may additionally be hydrogen;

$R_5$ is hydrogen; or $R_5$-$R_6$ together is —CH$_2$—CH$_2$—CH$_2$;

$R_6$ is hydrogen; $C_{1-7}$ alkyl; hydroxymethyl; mercaptomethyl; benzyl; or substituted benzyl;

$R_7$ and $R_8$ may be the same or different and are each independently COOR or CONR'R", where R is hydrogen or $C_{1-7}$ alkyl, and R' and R" are each independently hydrogen or $C_{1-3}$ alkyl;

when $R_2$ is $C_{1-10}$ alkyl, the stereochemistry at asymmetric center I can be either D or L;

when $R_6$ is not hydrogen, the stereochemistry at asymmetric center II is L; the stereochemistry at asymmetric center III is D.

The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, succinate, tartrate, thiocyanate, tosylate, and undecanoate. Also, the basic nitrogen-containing groups can be quaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-soluble or dispersible products are thereby obtained.

The compounds in the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in Freund's Complete Adjuvant. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific host protection against infectious organisms, for example, *Klebsiella pneumoniae, Candida albicans* or *Staphylococcus aureus.*

The term "substituted alkyl" for $R_1$ refers to an alkyl group of from 1 to 7 carbon atoms substituted by hydroxy, mercapto, alkoxy of 13 carbons, alkylmercapto of 13 carbons, hydroxy or mercapto esterified by an acid of 1–4 carbon atoms, halogen (F, Cl or Br), carboxyl, or carboxyl functionally modified by esterification with a lower alcohol of 1–3 carbons or by amidation. Preferably, the alkyl substituents are hydroxy or mercapto, either free or substituted by an alkyl group of 1–3 carbons.

The substituents in the term "substituted phenyl" for $R_1$ refer to the phenyl group substituted by one or more alkyl groups of 1–3 carbon atoms or hydroxy or mercapto groups either free, or etherified by an alkyl group of 1–3 carbons or esterified by an acid of 1–4 carbons, lower (1–4 C) alkyldioxy, cycloalkyldioxy of 5–7 carbon atoms, amino, trifluoromethyl, halo, or phenyl.

The substituents in the term "substituted phenyl" for $R_{11}$ are halo or phenyl.

For $R_7$ and $R_8$, among the optionally esterified carboxyl groups can be mentioned the carboxyl group esterified by a lower alcohol of 1–3 carbons, like methanol or ethanol. The carboxyl group can also be amidated, unsubstituted at the nitrogen atom or mono-or di-substituted with an alkyl, in particular, a lower alkyl, an aryl, particularly phenyl, or an aralkyl, particularly benzyl.

Most preferably, $R_1$ is alkyl of 1–3 carbons, phenyl or phenyl p-substituted by alkyl (1–3 C), amino, halogen, hydroxy or trifluoromethyl; $R_6$ is preferably hydrogen, alkyl of 1–4 carbons, hydroxymethyl, mercaptomethyl, benzyl or p-hydroxybenzyl; and preferably $R_5$ and $R_6$ together are —CH$_2$CH$_2$CH$_2$—.

The obtained compounds can be transformed to their salts in a classical fashion, for example, by reacting the acidic compounds obtained with alkaline or alkaline earth hydroxides or the basic compounds with acids.

The present invention is also directed to pharmaceutical preparations that contain a compound of Formula I. Among the pharmaceutical preparations relevant to this invention are salts that are administered by external route, for example, orally, rectally or parenterally to mammalian species. Preparations may be administered that contain the pharmacologically active compound by itself or mixed with a pharmaceutically acceptable carrier. The dose of the pharmacologically active compound depends on the animal specie, the age, and the state of the individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA-antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti-BSA antibodies by i.p. or subcutaneous application (s.c.) of 100–300 mg/kg/animal during 5 consecutive days (day 0 to day 4) after immunization with BSA.

The immunostimulatory effect of the compounds mentioned herein depend on the antigen, contrary to other bacterial immunostimulants (like LPS of *E. coli*). The injection of the compounds of the present invention results in augmentation of anti-BSA antibody titer only in mice immunized with BSA, and not with nonimmunized mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds of the present invention permit specific augmentation of humoral immunity, improve immune response, and provide long-lasting immunostimulatory effects on systemic activation of immune apparatus.

2. Stimulation of Mitotic Responses of Lymphocyte Cultures

Mouse lymphoid cells are cultured in microtiter plates, in RPMI-1640 medium with 2% fetal calf serum. Cultures are set in triplicates and consist of $3–5 \times 10^5$ spleen or $1.5 \times 10^6$ thymus cells per well in a final volume of 0.2 ml. Class specific mitogens are added at optimal or suboptimal concentrations, while control cultures are incubated without mitogens. The tested compounds are added shortly after the mitogens and the cultures are incubated for 48 hours at 37° with 5% $CO_2$. Incorporation of tritiated thymidine is determined after a pulse (1.0 $\mu$Ci/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose-dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore a remarkable therapeutic index.

The compounds of the present invention thus have the capacity, on the one hand, of being mixed with an antigen for which an increase in immunogenicity is required and on the other hand, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as (1) adjuvants by mixing them with vaccines with the goal of improving the effectiveness of the vaccination and (2) protective agents against infections caused by bacteria, viruses or pathogenic parasites, owing to immunity by humoral antibodies and/or to cellular mediation.

Thus, the described compounds are indicated, mixed with the most varied antigens, as adjuvants for experimental as well as industrial production of antisera for therapeutic and diagnostic purposes, as well as to induce immunologically active lymphocyte populations at the time of cell transfers.

Moreover, one can equally utilize the new compounds without simultaneously supplying antigen in order to enhance immune reactions that are already taking place in a subliminal fashion in a mammalian host. These compounds are therefore especially indicated for stimulation of individual immune defense, e.g., at the time of chronic or acute infections or in cases of selective (antigen-specific) immunological deficiencies as well as in situations of immune deficiency, but also acquired general deficiency (i.e., not antigen-specific) as appears with age, during initial shock from a grave illness, and before and soon after radiation therapy of immunosuppressive hormones. The said compounds can subsequently be administered in combination with anti-infectious antibiotics, chemical therapeutics or other methods of treatment, to combat immunological deficiencies. The described compounds are thus indicated equally for general prophylaxis of infectious disease in man and animal.

Intermediates for the compounds of Formula I may be prepared by condensing, using conventional procedures, a protected compound of Formula II with a protected compound of Formula III.

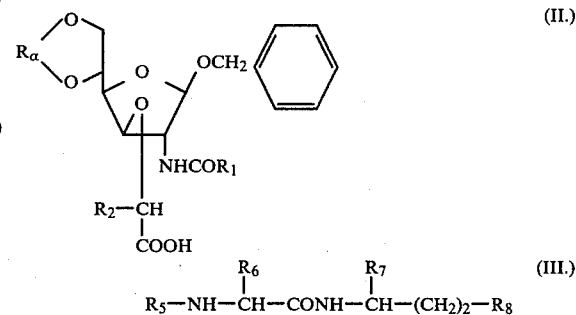

$$R_5-NH-\overset{R_6}{\underset{|}{CH}}-CONH-\overset{R_7}{\underset{|}{CH}}-(CH_2)_2-R_8 \quad (III.)$$

In the foregoing Formulas, $R_1$, $R_2$, $R_5$, $R_6$, $R_7$, and $R_8$ represent the groups mentioned above while $R_\alpha$ is an optionally substituted alkylidene radical that blocks the oxygen atoms at the C-5 and C-6 positions. Among the alkylidene radicals, particularly suitable are the lower alkylidene radicals, especially ethylidene, isopropylidene, propylidene, or cycloalkylidene, especially cyclopentylidene, or cyclohexylidene, and also, the optionally substituted benzylidene radical, preferentially substituted at the para position. As protecting group for the carboxyl in the dipeptide of Formula III, there may be mentioned tertiary-butyl, benzyl, or benzhydryl. The protecting group may be any suitable to protect the group to which it is attached during the condensation reaction, and which may be readily removed thereafter.

The condensation is effected by reacting the compound of Formula II in the form where the carboxylic acid is activated, with the amino compound of Formula III. The activated carboxyl group may be, for example, an acid anhydride, preferably, a mixed acid anhydride like an acetate of the acid, an amide of the acid like an imidasolid, an isoxazolid or an activated ester. The activated esters, include the cyanomethyl ester, the carboxylmethyl ester, the p-nitrophenyl thioester, the p-nitrophenyl ester, the 2,4,5-trichlorophenyl ester, the pentachlorophenyl ester, the N-hydroxysuccinimide ester, the N-hydroxyphthalimide ester, the 8-hydroxyquinoline ester, the 2-hydroxy-1,2-dihydro-1-carboethoxyquinoline esters, the N-hydroxypiperidine ester or enol ester derived from N-ethyl-5-phenyl-isoxazolium-3′-sulfonate. The activated esters may equally be obtained from a carbodiimide by addition of N-hydroxysuccinimide or from a substituted 1-hydroxybenzyltriazole for example, a halogen, methyl, or methoxy-substituted 3-hydroxy-4-oxo-3,4-dihydrobenzo[d]-1,2,3-triazine.

The amino group may be activated, for example, by reaction with a phosphitamide.

Among the methods of reaction with the activated esters, one must mention in particular those that involve N-ethyl-5-phenyl-isoxazolium-3′-sulfonate (Woodward's Reagent K), N-ethoxy-carbonyl-2-ethoxy-1,2-dihydroquinoline, or carbodiimide.

The starting materials utilized are known or can be made in a known fashion. Thus, one can obtain compounds of Formula II, for example, by reacting the corresponding sugar unsubstituted at position-3 with a halogen-$R_2$ acetic acid where $R_2$ has the meaning mentioned above. The ether is obtained in the presence of a strong base. The halogen is preferentially bromo or chloro.

Another process of synthesizing intermediates for the compounds of Formula I consists of condensation of a protected compound of Formula IV:

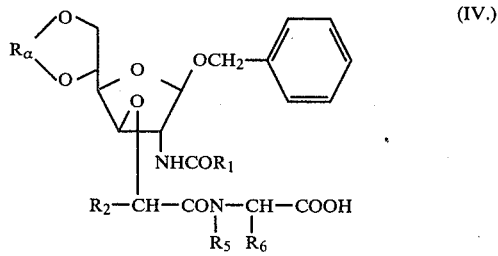

(IV.)

wherein $R_1$, $R_2$, $R_5$, $R_6$, and $R_{60}$ have the meaning mentioned above, with a compound of Formula V:

$$H_2N-\overset{R_7}{\underset{|}{CH}}-(CH_2)_2-R_8,$$ (V.)

wherein $R_7$ and $R_8$ have the meaning mentioned above.

The condensation may be effected by reacting a compound of Formula IV in the form of an activated carboxylic acid, with the amino compound of Formula V, or by reacting the Formula IV compound in the form of the free C-terminal carboxyl group with the Formula V compound where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino group may be activated, for example, by reaction with a phosphitamide. The readily removable protecting groups correspond to those mentioned above.

The starting materials are obtained in classical fashion. One can, therefore, react the corresponding sugar unsubstituted at position-3 with halogen-$R_2$-acetamido-$R_6$-acetic acid or a compound of Formula II with an amino-$R_6$-acetic acid where the carboxyl group is blocked as mentioned above.

Another process for inserting the side chain at position-3 of the sugar radical consists in reacting a compound having the following structure:

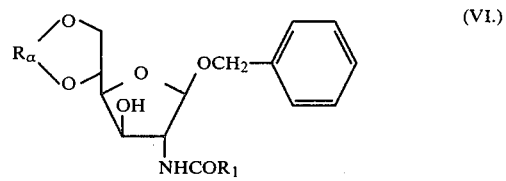

(VI.)

where $R_1$ and $R_\alpha$ have the meaning mentioned above, with a compound of formula VII:

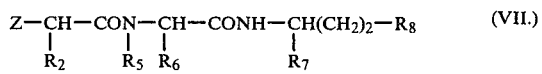

(VII.)

where Z represents an esterified hydroxy group capable of reacting and wherein $R_2$, $R_5$, $R_6$, $R_7$ and $R_8$ have the meaning given above. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. The starting materials utilized are known or can be made in a known fashion.

Condensations of (a) protected compounds of Formula II with a protected compound of Formula III; (b) protected compound of Formula IV with a protected compound of Formula V; or (c) a protected compound of Formula VI with a protected compound of Formula VII, afford intermediates of Formula VIII:

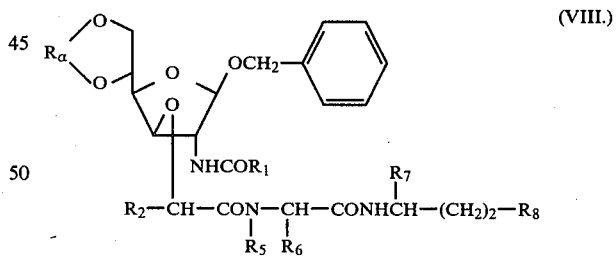

(VIII.)

wherein $R_1$, $R_2$, $R_5$, $R_6$, $R_7$, $R_8$, and $R_\alpha$ have the meanings mentioned above.

Intermediates of Formula VIII are converted into compounds of Formula I by selective removal of $R_\alpha$, acylation of the C-5 and C-6 hydroxyls, and final removal of the remaining protecting groups by hydrogenolysis with hydrogen in the presence of a noble metal catalyst.

$R_\alpha$ is removed by acid hydrolysis to give intermediates of Formula IX, which is effected in a classical fashion, for example, with acidic ion-exchange resins, in particular, with an exchange resin containing sulfonic acid groups, e.g. Amberlite IR-120 (resins of styrene containing strongly acidic sulfonyl groups) or Dowex- 50 (polystyrene sulfonic acids); or with a strong inorganic or organic acid, e.g. hydrochloric acid, hydrobromic acid, sulfuric acid, a sulfonic acid, e.g. methanesulfonic acid, a phenylsulfonic acid optionally substituted in its aromatic nucleus, e.g. p-toluenesulfonic acid, or a carboxylic acid, e.g. acetic acid or trifluoroacetic acid:

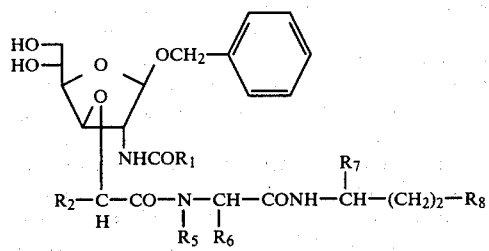

(IX.)

The compounds of Formula I are then prepared by reaction of the intermediates of Formula IX described above with the appropriate acid whereby condensation results in the desired 6-O- and/or 5-O- substituted compounds. All of the appropriate acids for preparing the compounds of Formula I are known compounds or may be prepared by known methods in an obvious manner. The condensation reaction will initially take place preferentially at the 6-position of the glucofuranose ring. Then the reaction conditions are driven with the same or a different acid giving rise to 5-O, 6-O-diacylated derivatives wherein the acyl groups are the same or different. Where it is desired to prepare only the 5-O-acylated derivatives, the 6-position must be blocked while the 5-position substitution is carried out, followed be deblocking. The blocking and deblocking reactions may be carried out in accordance with procedures well-known in the art.

The condensation reactions may be carried out in accordance with procedures well established in the art for preparing organic compounds. Thus, the condensation may be carried out using the carboxylic acid, the acid anhydride, or the acid halide.

Where the carboxylic acid is utilized, a coupling agent, for example N,N'-dicyclohexylcarbodiimide (DCC) in the presence of 4-dimethylaminopyridine (DMAP), will be employed. The reaction is carried out in an inert aprotic solvent, such as dimethylformamide, dimethylsulfoxide, or pyridine, at a temperature of from 0° to 50° C. for from 6 hours to 6 days.

Where the acid anhydride is utilized, a coupling agent may be employed, although this is not necessary. However, an acid acceptor, such as pyridine, 4-dimethylaminopyridine, or triethylamine should be used. The solvent medium in which the reaction is carried out and the other reaction conditions are the same as for the carboxylic acid condensation.

Where the acid halide is utilized, all of the reaction conditions are the same as those for the acid anhydride condensation.

Once the condensation reaction has been completed, the remaining protecting groups are readily removed by hydrogenolysis, preferably carried out with a catalyst such as palladium oxide in the presence of glacial acetic acid.

Compounds wherein $R_1$ is other than methyl are obtained by reacting 2-amino-2-deoxy-D-glucose, in the case where $R_1$ is alkyl or substituted-alkyl, with the appropriate alkanoic anhydride or alkanoyl halide, preferably chloride, or substituted-alkanoic anhydride or substituted-alkanoyl halide, preferably chloride, and in the case where $R_1$ is phenyl or substituted-phenyl, with the appropriate aroic anhydride or aroyl halide, preferably chloride, or substituted aroic anhydride or substituted aroyl halide, preferably chloride, in the presence of an appropriate acid acceptor, such as pyridine or triethylamine. The protecting groups are then introduced at the C-1, C-5, and C-6 positions to give a compound of Formula VI which may then be converted to a compound of Formula II or Formula IV.

Compounds wherein $R_6$ is other than methyl, may be obtained when, for example, one of the following amino acids is substituted for alanine:

| Amino acid | $R_6$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_5$ and $R_6$ together are $-CH_2CH_2CH_2-$ are obtained by substituting proline for alanine.

EXAMPLE 1

Preparation of 2-Acetamido-5,6-di-O-acetyl-2-deoxy-3-O-(D-2-propionyl-L-alanyl-D-isoglutamine)-D-glucofuranose Step A: Preparation of benzyl 2-acetamido-3-O-(D-1-carboxyethyl)-2-deoxy-5,6-O-isopropylidene-β-D-glucofuranoside To a stirred solution of benzyl 2-acetamido-2-deoxy-5,6-O-isopropylidene-β-D-glucofuranoside [prepared by the process set forth in A. Hasegawa, T. Sakurai, & N. Hasegawa, Carbohydr. Res., 45(1975) 19–27](1.88 g., 5.35 mmol) in dry p-dioxane (75 ml.) was added sodium hydride in oil suspension (1.0 g.) (50% of sodium hydride by weight). The mixture was stirred at 95° C. and additional dioxane (70 ml.) was added to break up the gel that formed after addition of the sodium hydride. After 1 hr., the temperature was lowered to 65° C., and a solution of L-2-chloropropionic acid (1.16 g., 10.7 mmol) in a small volume of dioxane (3 ml.) was added. The reaction mixture was stirred overnight at 65° C., cooled, and excess sodium hydride decomposed by careful dropwise addition of water (100 ml.). The resulting mixture was partially concentrated and extracted with chloroform. The aqueous layer was cooled in an ice-bath and acidified to pH3 with 2.5 M hydrochloric acid. The mixture was immediately extracted with chloroform three times and the combined organic extracts dried over sodium sulfate. Evaporation of the filtered solution gave benzyl 2-acetamido-3-O-(D-1-carboxyethyl)-2-deoxy-5,6-O-isopropylidene-β-D-glucofuranoside as a slightly colored gummy solid; yield 1.92 g. (85%). The 300 MHz NMR spectrum in dimethylsulfoxide -d-6 was in accord with the desired structure.

Step B: Preparation of benzyl 2-acetamido-2-deoxy-5,6-O-isopropylidene-3-O-(D-2-propionyl-L-alanyl-D-isoglutamine benzyl ester)-β-D-glucofuranoside To a solution of benzyl 2-acetamido-3-O-(D-1-carboxyethyl)-2-deoxy-5,6-O-isopropylidene-β-D-glucofuranoside (1.88 g., 4.44 mmol) in dry N,N-dimethylformamide (15 ml.) at −15° C. were added successively N-methylmorpholine (0.49 ml.) and isobutyl chloroformate (0.58 ml.). After stirring 5 min. at 15° C., a precooled solution of L-alanyl-D-isoglutamine benzyl ester hydrochloride (1.53 g., 4.45 mmol) and N-methylmorpholine (0.49 ml.) in dry N,N-dimethylformamide (10 ml.) was added. The mixture was stirred for 4 hrs. at −15° C. with exclusion of moisture. After the temperature was increased to 0° C., 2.5 M aqueous potassium hydrogencarbonate (8 ml.) was added, and the mixture was stirred for 30 min. at 0° C. Since no precipitation of product occurred upon addition of water (200 ml.), the mixture was brought to pH7 with 2.5 M hydrochloric acid. After evaporation, the residue was partitioned between chloroform and water, the combined organic extracts washed with water, dried over magnesium sulfate, and evaporated to a syrup that was dissolved in the minimal volume of chloroform. The solution was applied to a column of silica gel (Merck No. 7734) that was eluted with initially 24:1 and subsequently 9:1 chloroform-methanol. The fractions containing the desired product were combined and evaporated to a syrup that solidified upon trituration with diethyl ether. The amorphous solid was filtered and dried in vacuo to afford benzyl 2-acetamido-2-deoxy-5,6-O-isopropylidene-3-O-(D-2-propionyl-L-alanyl-D-isoglutamine benzyl ester(-β-D-glucofuranoside; yield 2.0 g. (63%); $[\alpha]_D -61°$ (c 1, chloroform). The 300 MHz NMR spectrum in dimethylsulfoxide-d$_6$ was in accord with the desired structure.

Analysis: Calculated for $C_{36}H_{48}N_4O_{11}\cdot\frac{1}{2}$ H$_2$O (721.82): C,59.90; H, 6.84; N, 7.76. Found: C, 59.68; H, 6.74; N, 7.82.

Step C: Preparation of benzyl 2-acetamido-2-deoxy-3-O-(D-2-propionyl-L-alanyl-D-isoglutamine benzyl ester)-β-D-glucofuranoside A mixture of benzyl 2-acetamido-2-deoxy-5,6-O-isopropylidene-3-O-(D-2-propionyl-L-alanyl-D-isoglutamine benzyl ester)-β-D-glucofuranoside (1.8 g., 2.5 mmol) in 65% aqueous acetic acid (100 ml.) was stirred at 40° C. until thin layer chromatography investigation (9:1 chloroform-methanol as developing system) indicated complete conversion to a slower-moving material. The mixture was then evaporated, with traces of acetic acid being removed by several coevaporations with toluene. The residue was triturated with diethyl ether, the resulting solid filtered, washed with ether and dried in vacuo over phosphorous pentoxide to afford benzyl 2-acetamido-2-deoxy-3-O-(D-2-propionyl-L-alanyl-D-isoglutamine benzyl ester)-β-D-glucofuranoside as an amorphous solid; yield 1.63 g. (96%); $[\alpha]_D -73°$ (c 1, chloroform). The 300 MHz NMR spectrum in dimethylsulfoxide-d$_6$ was in accord with the desired structure.

Analysis: Calculated for $C_{33}H_{44}N_4O_{11}\frac{1}{2}$ H$_2$O (681.75): C, 58.14; H, 6.65; N, 8.22. Found: C, 57.91, H, 6.49; N, 8.15.

Step D: Preparation of benzyl 2-acetamido-5,6-di-O-acetyl-2-deoxy-3-O-(D-2-propionyl-L-alanyl-D-isoglutamine benzyl ester)-β-D-glucofuranoside To a solution of benzyl 2-acetamido-2-deoxy-3-O-(D-2-propionyl-L-alanyl-D-isoglutamine benzyl ester)-β-D-glucofuranoside (500 mg., 0.74 mmol) in dry pyridine (6 ml.) at room temperature was added acetic anhyride (4 ml.). The mixture was kept at room temperature until thin layer chromatography investigation (9:1 chloroformmethanol as developing system) indicated complete conversion to a faster-moving material. The formation of intermediate mono-O-acetates was observed. The mixture was then evaporated and coevaporated several times with toluene. The residue was dissolved in the minimal volume of chloroform and the solution passed through a short column of silica gel (Merck No. 7734) to remove small amounts of impurities. Benzyl 2-acetamido-5,6-di-O-acetyl-2-deoxy-3-O-(D-2-propionyl-L-alanyl-D-isoglutamine benzyl ester)-β-D-glucofuranoside was crystallized from ethanol-diethyl ester; yield 377 mg. (67%); m.p. 164°–166° C., $[\alpha]_D -69°$ (c 1, chloroform). The 300 MHz NMR spectrum in dimethylsulfoxide-d$_6$ was in accord with the desired structure.

Analysis: Calculated for $C_{37}H_{48}N_4O_{13}$ (756.8): C, 58.72; H, 6.39; N, 7.40. Found: C, 58.33; H, 6.41; N, 7.45.

Step E: Preparation of 2-acetamido-5,6-di-O-acetyl-2-deoxy-3-O-(D-2-propionyl-L-alanyl-D-isoglutamine)-D-glucofuranose A solution of benzyl 2-acetamido-5,6-di-O-acetyl-2-deoxy-3-O-(D-2-propionyl-L-alanyl-D-isoglutamine benzyl ester)-β-D-glucofuranoside (200 mg., 0.26 mmol) in glacial acetic acid (5 ml.) was hydrogenolyzed overnight at atmospheric pressure and room temperature in the presence of palladium (added as PdO, 200 mg.). The reaction mixture was filtered through Celite, the filtrate evaporated, and coevaporated several times with water and finally with toluene. The residue was taken up in a small volume of methanol, filtered to remove undissolved materials, and the product precipitated by addition of diethyl ether. The solid was filtered, washed with ether, and dried in vacuo over phosphorous pentoxide. The solid was dissolved in water and lyophilized to afford 2-acetamido-5,6-di-O-acetyl-2-deoxy-3-O-(D-2-propionyl-L-alanyl-D-isoglutamine)-D-glucofuranose as a white amorphous solid; yield 130 mg. (86%). The 300 MHz NMR spectrum in deuterium oxide was in accord with the desired structure.

EXAMPLE 2

Preparation of 2-acetamido-5-O-acetyl-2-deoxy-3-O-(D-2-propionyl-L-alanyl-D-isoglutamine)-6-O-stearoyl-D-glucofuranose

Step A: Preparation of benzyl 2-acetamido-5-O-acetyl-2-deoxy-3-O-(D-2-propionyl-L-alanyl-D-isoglutamine benzyl ester)-6-O-stearoyl-β-D-glucofuranoside To a solution of benzyl 2-acetamido-2-deoxy-3-O-(D-2-propionyl-L-alanyl-D-isoglutamine benzyl ester)-β-D-glucofuranoside (250 mg., 0.37 mmol) in dry pyridine (10 ml.) was added stearoyl chloride (0.31 ml., 0.93 mmol). The reaction mixture was stirred for 18 hrs. at room temperature with exclusion of moisture and then treated with an excess of acetic anhydride for 24 hrs. at room temperature. The mixture was then evaporated and coevaporated several times with toluene. The residue was dissolved in the minimal volume of chloroform, and the solution was applied to a column of silica gel (Merck No. 7734) and elution was effected with 30:1 chloroform/methanol. Further purification was achieved by thick-layer chromatography on plates (1.000 mm) of silica gel GF$_{254}$ (Analtech) with 9:1 chloroform-methanol as the developant, and extraction with ethyl acetate. Evaporation gave a chromatographically homogeneous solid that was hydrogenolyzed as described in Step B. The 300 MHz NMR spectrum in dimethylsulfoxide-d$_6$ was in accord with the desired structure.

Step B: Preparation of 2-acetamido-5-O-acetyl-2-deoxy-3-O-(D-2-propionyl-L-alanyl-D-isoglutamine)-6-O-stearoyl-D-glucofuranose A solution of the solid obtained in Step A in glacial acetic acid (5 ml.) was hydrogenolyzed for 18 hrs. at atmospheric pressure and room temperature in the presence of palladium (added as PdO, 150 mg.). The reaction mixture was filtered through Celite, the filtrate evaporated, and coevaporated several times with water and finally with toluene. The residue was triturated with diethyl ether, the solid filtered, washed with ether, and dried in vacuo over phosphorous pentoxide. 2-Acetamido-5-O-acetyl-2-deoxy-3-O-(D-2-propionyl-L-alanyl-D-isoglutamine)-6-O-stearoyl-D-glucofuranose was obtained as an amorphous solid; yield 22 mg. (7.4% based on benzyl 2-acetamido-2-deoxy-3-O-(D-2-propionyl-L-alanyl-D-isoglutamine benzyl ester)-β-D-glucofuranoside). The 300 MHz NMR spectrum in dimethylsulfoxide-d$_6$ was in accord with the desired structure.

EXAMPLE 3

Preparation of 2-acetamido-5-O-acetyl-6-O-behenoyloxyisobutyryl-2-deoxy-3-O-(D-2-propionyl-L-alanyl-D-isoglutamine)-D-glucofuranose

Step A: Preparation of benzyl 2-acetamido-6-O-behenoyloxyisobutyryl-2-deoxy-3-O-(D-2-propionyl-L-alanyl-D-isoglutamine benzyl ester)-β-D-glucofuranoside To a solution of behenoyloxyisobutyric acid (159 mg. 0.37 mmol) in dry N,N-dimethylformamide (4 ml.) was added 4-dimethylaminopyridine (5 mg.) and benzyl 2-acetamido-2-deoxy-3-O-(D-2-propionyl-L-alanyl-D-isoglutamine benzyl ester)-β-D-glucofuranoside (250 mg., 0.37 mmol). The mixture was cooled in an ice-bath and N,N'-dicyclohexylcarbodiimide (DCC) (77 mg.) was added. The reaction mixture was stirred overnight at room temperature. Dichloromethane was added to the mixture to achieve solution. A second addition of behenoyloxyisobutyric acid (159 mg.) and DCC (77 mg.) was made and the mixture stirred overnight at room temperature. Again sufficient dichloromethane was added to cause solution. After a third addition of the acid and DCC and stirring overnight at room temperature, the reaction mixture was concentrated, the solid taken up in dichloromethane, washed twice with 0.5 M hydrochloric acid, once with saturated aqueous sodium bicarbonate, the organic layer filtered and dried (sodium sulfate). The solid obtained upon evaporation was dissolved in the minimal volume of chloroform, and the solution was applied to a column of silica gel (Merck No. 7734) that was eluted with 30:1 chloroform-methanol. Evaporation of the appropriate fractions gave benzyl 2-acetamido-6-O-behenoyloxyisobutyryl-2-deoxy-3-O-(D-2-propionyl-L-alanyl-D-isoglutamine benzylester)-β-D-glucofuranoside as a solid; yield 80 mg. (20%).

Step B: Preparation of benzyl 2-acetamido-5-O-acetyl-6-O-behenoyloxyisobutyryl-2-deoxy-3-O-(D-2-propionyl-L-alanyl-D-isoglutamine benzyl ester) β-D-glucofuranoside To a solution of benzyl 2-acetamido-6-O-behenoyloxyisobutyryl-2-deoxy-3-O-(D-2-propionyl-L-alanyl-D-isoglutamine benzyl ester)-β-D-glucofuranoside (80 mg.) in dry pyridine (1 ml.) was added acetic anhydride (0.6 ml.). The reaction mixture was allowed to stand overnight at room temperature, evaporated, and coevaporated several times with toluene. The residue was dissolved in the minimal volume of chloroform and the solution applied to a column of silica gel (Merck No. 7734) that was eluted with 35:1 chloroform-methanol. The appropriate fractions were combined and evaporated to give benzyl 2-acetamido-5-O-acetyl-6-O-behenoyloxyisobutyryl-2-deoxy-3-O-(D-2-propionyl-L-alanyl-D-isoglutamine benzyl ester)-β-D-glucofuranoside as a solid; yield 73 mg. (88%). The 300-MH$_z$ NMR spectrum in dimethylsulfoxide-d$_6$ was in accord with the desired structure.

Step C: Preparation of 2-acetamido-5-O-acetyl-6-O-behenoyloxyisobutyryl-2-deoxy-3-O-(D-2-propionyl-L-alanyl-D-isoglutamine)-D-glucofuranose A solution of benzyl 2-acetamido-5-O-acetyl-6-O-behenoyloxyisobutyryl-2-deoxy-3-O-(D-2-propionyl-L-alanyl-D-isoglutamine benzyl ester)-β-D-glucofuranoside (70 mg.) in glacial acetic acid (5 ml.) was hydrogenolyzed for 24 hrs. at atmospheric pressure and room temperature in the presence of palladium (added as PdO, 110 mg.). The reaction mixture was filtered through Celite, the filtrate evaporated, and coevaporated several times with toluene. The residue was applied to a column of silica gel (Merck No. 7734) that was eluted with initially 9:1 chloroform-methanol and subsequently 80:20:2 chloroform-methanol-water. Evaporation of the appropriate fractions gave a solid that was dried in vacuo over phosphorous pentoxide. 2-Acetamido-5-O-acetyl-6-O-behenoyloxyisobutyryl-2-deoxy-3-O-(D-2-propionyl-L-alanyl-D-isoglutamine)-D-glucofuranose was obtained in 54% yield (32 mg.). The 300-MHz NMR spectrum in dimethylsulfoxide-d$_6$ was in accord with the desired structure.

What is claimed is:

1. Dipeptidyl 5-O, 6-O-acyl-2-amino-2-deoxy-D-glucofuranoses of the general structural formula:

15

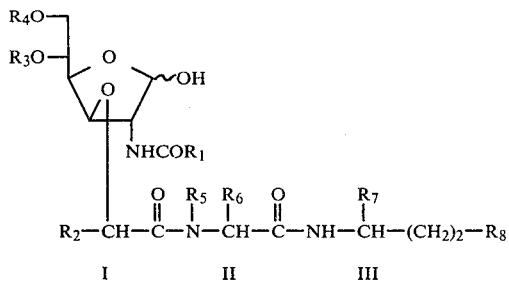
(I.)

wherein

R₁ is $C_{1-7}$ alkyl, substituted $C_{1-7}$ alkyl; phenyl; or substituted phenyl;

wherein the substituent is one or more alkyl groups of 1-3 carbon atoms or hydroxy or mercapto groups either free, or esterified by an alkyl group of 1-3 carbons or esterified by an acid of 1-4 carbons, lower (1-4$_C$) alkyldioxy cycloalkyldioxy of 5-7 carbon atoms, amino, trifluoromethyl, halo, or phenyl;

R₂ is hydrogen; or $C_{1-10}$ alkyl;

R₃ and R₄ may be the same or different and are each independently acyl of the formula:

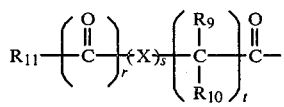

where
X is —O—, —S—, or

R₉, R₁₀, and R₁₂ may be the same or different and are each independently hydrogen; $C_{1-20}$ alkyl; $C_{1-20}$ alkylcarbonyloxy; amino; benzyl; $C_{1-20}$ alkoxymethyl; or $C_{1-20}$ alkylamido;

r is 0 or 1; s is 0 or 1; and t is 0-20, provided that s may only be 0 when r and t are greater than 0, or when r is 0 and R₁₁ is amino, phenyl, substituted phenyl, 1-adamantyl, or heterocycle selected from the group consisting of 2- or 3-furyl, 2- or 3-thienyl, 2- or 3-pyrrolidinyl, 2-, 3-, or 4-pyridyl, and 1-tetrazolyl, said heterocycle optionally substituted with $C_{1-20}$ alkylcarbonyl; and

16

R₁₁ is hydrogen; $C_{1-30}$ alkyl; $C_{2-30}$ alkenyl; $C_{1-30}$ alkoxy; phenyl; $C_{1-20}$ alkylsulfonyl; or cholesteryl; and R₄ may additionally be hydrogen;

R₅ is hydrogen; or R₅-R₆ together is —CH₂—CH₂—CH₂;

R₆ is hydrogen; $C_{1-7}$ alkyl; hydroxymethyl; mercaptomethyl; benzyl; or substituted benzyl;

R₇ and R₈ may be the same or different and are each independently COOR or CONR'R", where R is hydrogen or $C_{1-7}$ alkyl, and R' and R" are each independently hydrogen or $C_{1-3}$ alkyl;

when R₂ is $C_{1-10}$ alkyl, the stereochemistry at asymmetric center I can be either D or L;

when R₆ is not hydrogen, the stereochemistry at asymmetric center II is L; the stereochemistry at asymmetric center III is D.

2. A compound according to claim 1 wherein the compound is 2-acetamido-5,6-di-O-acetyl-2-deoxy-3-O-(D-2-propionyl-L-alanyl-D-isoglutamine)-D-glucofuranose.

3. A compound according to claim 1 wherein the compound is 2-acetamido-5-O-acetyl-2-deoxy-3-O-(D-2-propionyl-L-alanyl-D-isoglutamine)-6-O-stearoyl-D-glucofuranose.

4. A compound according to claim 1 wherein the compound is 2-acetamido-5-O-acetyl-6-O-behenoyloxyisobutyryl-2-deoxy-3-O-(D-2-propionyl-L-alanyl-D-isoglutamine)-D-glucofuranose.

5. A composition comprising a compound of claim 1 present in an amount effective to produce an immunostimulatory effect and a vaccine against bacterial, viral or parasitic infections or against tissue antigens of normal or pathogenic origin.

6. A composition according to claim 5 wherein the compound is 2-acetamido-5,6-di-O-acetyl-2-deoxy-3-O-(D-2-propionyl-L-alanyl-D-isoglutamine)-D-glucofuranose.

7. A composition according to claim 5 wherein the compound is 2-acetamido-5-O-acetyl-2-deoxy-3-O-(D-2-propionyl-L-alanyl-D-isoglutamine)-6-O-stearoyl-D-glucofuranose.

8. A composition according to claim 5 wherein the compound is 2-acetamido-5-O-acetyl-6-O-behenoyloxyisobutyryl-2-deoxy-3-O-(D-2-propionyl-L-alanyl-D-isoglutamine)-D-glucofuranose.

9. A composition according to claim 5 wherein the compound is present in an amount effective to exert an adjuvant effect.

10. An antibacterial composition comprising a pharmaceutically acceptable carrier and an effective amount of a compound of claim 1.

* * * * *